(12) United States Patent
Clawson (10) Patent No.: US 7,993,071 B2
(45) Date of Patent: Aug. 9, 2011

(54) ASSEMBLIES FOR COUPLING TWO ELEMENTS AND COUPLED ASSEMBLIES

(75) Inventor: Burrell E. Clawson, Newport Beach, CA (US)

(73) Assignee: Burrell E. Clawson, Newport Beach, CA (US)

( * ) Notice: Subject to any disclaimer, the term of this patent is extended or adjusted under 35 U.S.C. 154(b) by 0 days.

(21) Appl. No.: 11/586,963

(22) Filed: Oct. 25, 2006

(65) Prior Publication Data
US 2008/0101856 A1    May 1, 2008

(51) Int. Cl.
*B65D 53/02* (2006.01)
(52) U.S. Cl. ......... 403/364; 403/267; 403/288; 277/641
(58) Field of Classification Search .................. 403/288, 403/291, 339, 364, 267; 277/630, 631, 637, 277/641; 220/615, 617, 621, 783, 790, 795
See application file for complete search history.

(56) References Cited

U.S. PATENT DOCUMENTS

| | | | |
|---|---|---|---|
| 294,244 A | 2/1884 | Lewis et al. ................... 210/445 |
| 604,931 A | 5/1898 | Eisendrath .................... 210/445 |
| 973,723 A | 10/1910 | Thomson ..................... 210/445 |
| 1,454,836 A | 8/1921 | Slocomb | |
| 2,766,796 A | 10/1956 | Tupper | |
| 2,839,229 A | 6/1958 | Scheswohl | |
| 2,882,947 A | 4/1959 | Close | |
| 2,912,982 A | 11/1959 | Barsky ......................... 128/207 |
| 3,355,056 A | 11/1967 | Fisch | |
| 3,446,391 A | 5/1969 | Yates | |
| 3,527,372 A | 9/1970 | Manning | |
| 3,572,413 A * | 3/1971 | Livingstone .................. 220/782 |
| 3,612,048 A | 10/1971 | Takaoka et al. ............... 128/205 |
| 3,615,233 A | 10/1971 | Doering et al. ............... 128/205 |
| 3,721,238 A | 3/1973 | Wise et al. .................... 128/188 |
| 3,747,598 A | 7/1973 | Cowans ........................ 128/142 |
| 3,782,081 A | 1/1974 | Munters ......................... 55/278 |
| 3,782,083 A | 1/1974 | Rosenberg .................... 128/205 |
| 3,912,795 A | 10/1975 | Jackson ...................... 261/36 R |
| 3,932,153 A | 1/1976 | Byrns ............................. 55/511 |
| 4,030,850 A * | 6/1977 | Hyde ............................ 403/288 |
| 4,036,616 A | 7/1977 | Byrns ............................. 55/498 |
| 4,040,804 A | 8/1977 | Harrison ........................ 55/158 |
| 4,046,282 A * | 9/1977 | Ruch ............................ 220/270 |
| 4,054,134 A | 10/1977 | Kritzer ......................... 128/205 |
| 4,063,913 A | 12/1977 | Kippel et al. ................... 55/274 |
| 4,079,857 A * | 3/1978 | Crisci ........................... 206/508 |
| 4,090,513 A | 5/1978 | Togawa ........................ 128/212 |
| 4,091,953 A | 5/1978 | Daenen ..................... 220/23.86 |
| 4,108,172 A | 8/1978 | Moore, Jr. .................... 128/188 |
| 4,133,656 A | 1/1979 | Kippel et al. ................... 55/274 |
| 4,128,732 A | 4/1979 | Burrow et al. ................ 210/232 |

(Continued)

FOREIGN PATENT DOCUMENTS

EP    0 322 790    7/1989

(Continued)

*Primary Examiner* — Joshua T Kennedy
(74) *Attorney, Agent, or Firm* — Stout, Uxa, Buyan & Mullins; Frank J. Uxa (57) ABSTRACT

Assemblies for coupling together two elements are provided and include a first coupling member and a second coupling member. The second coupling member has a body sized and adapted to be fitted into a hollow space defined by the first coupling member. The coupling members are structured to deflect the body of the second coupling member toward a first wall of the first coupling member as the body is passed into the hollow space.

24 Claims, 5 Drawing Sheets

U.S. PATENT DOCUMENTS

| | | | | |
|---|---|---|---|---|
| 4,166,548 A | 9/1979 | Crisci | | 220/308 |
| 4,168,706 A | 9/1979 | Lovell et al. | | 128/142 R |
| 4,171,962 A | 10/1979 | Kippel et al. | | 55/274 |
| 4,172,709 A | 10/1979 | Kippel et al. | | 55/274 |
| 4,181,511 A | 1/1980 | Kippel et al. | | 55/274 |
| 4,181,512 A | 1/1980 | Kippel et al. | | 55/274 |
| 4,192,301 A | 3/1980 | Hardwick | | 128/205 |
| 4,200,094 A | 4/1980 | Gedeon et al. | | 128/201.13 |
| 4,224,939 A | 9/1980 | Lang | | 128/205.13 |
| 4,234,326 A | 11/1980 | Bailey et al. | | 55/278 |
| 4,297,117 A | 10/1981 | Holter et al. | | 55/389 |
| 4,325,364 A | 4/1982 | Evans | | 128/201 |
| 4,327,717 A | 5/1982 | Oetjen et al. | | 128/201.13 |
| 4,335,827 A * | 6/1982 | Knize et al. | | 220/284 |
| 4,360,018 A | 11/1982 | Choksi | | 128/205.12 |
| 4,367,734 A | 1/1983 | Benthin | | 128/204.13 |
| 4,380,304 A * | 4/1983 | Anderson | | 220/782 |
| 4,382,440 A | 5/1983 | Kapp et al. | | 128/205 |
| 4,444,332 A | 4/1984 | Widén et al. | | 220/306 |
| 4,453,646 A | 6/1984 | Harrild | | 220/258 |
| 4,458,679 A | 7/1984 | Ward | | 128/201.13 |
| 4,516,573 A | 5/1985 | Gedeon | | 128/201.13 |
| 4,558,696 A | 12/1985 | Eiserman et al. | | 128/205.12 |
| 4,561,562 A | 12/1985 | Trombly | | 220/306 |
| 4,597,917 A | 7/1986 | Lunsford | | 261/153 |
| 4,687,235 A | 8/1987 | Stoll | | 285/281 |
| 4,707,167 A | 11/1987 | Saito et al. | | 55/267 |
| 4,708,259 A * | 11/1987 | Olimpio | | 220/790 |
| 4,762,248 A * | 8/1988 | Uhlig | | 206/508 |
| 4,771,770 A | 9/1988 | Artemenko et al. | | 128/201.13 |
| 4,790,327 A | 12/1988 | Despotis | | 128/719 |
| 4,790,832 A | 12/1988 | Lopez | | 128/912 |
| 4,809,868 A | 3/1989 | Pomroy | | 220/260 |
| 4,829,997 A | 5/1989 | Douwens et al. | | 128/201.13 |
| 4,979,370 A | 12/1990 | Cassel | | 220/306 |
| 4,981,233 A | 1/1991 | Scheurer | | 220/212 |
| 5,016,628 A | 5/1991 | Lambert | | 128/205.28 |
| 5,022,394 A | 6/1991 | Chmielinski | | 128/207.14 |
| 5,035,236 A | 7/1991 | Kanegaonkar | | 128/201.13 |
| 5,038,767 A | 8/1991 | Jumpertz | | 128/202.26 |
| 5,109,471 A | 4/1992 | Lang | | 392/396 |
| 5,133,470 A | 7/1992 | Abrams et al. | | 215/250 |
| 5,143,060 A | 9/1992 | Smith | | 128/205 |
| 5,172,686 A | 12/1992 | Anthony | | 128/203.16 |
| 5,195,527 A | 3/1993 | Hicks | | 128/203 |
| 5,213,096 A | 5/1993 | Kihlberg et al. | | 128/205.12 |
| 5,222,746 A * | 6/1993 | Van Steenbrugge | | 277/630 |
| 5,228,435 A | 7/1993 | Smith | | 128/205.12 |
| 5,230,727 A | 7/1993 | Pound et al. | | 55/492 |
| 5,255,674 A | 10/1993 | Oftedal et al. | | 128/203.16 |
| 5,275,287 A * | 1/1994 | Thompson | | 215/344 |
| 5,320,096 A | 6/1994 | Hans | | 128/205.29 |
| 5,333,607 A | 8/1994 | Kee et al. | | 128/292 |
| 5,337,739 A | 8/1994 | Lehman | | 128/205.27 |
| 5,348,549 A | 9/1994 | Brown et al. | | 604/403 |
| 5,349,946 A | 9/1994 | McComb | | 128/203 |
| 5,360,002 A | 11/1994 | Smith | | 128/205.28 |
| 5,377,860 A | 1/1995 | Littlejohn et al. | | 220/306 |
| 5,383,447 A | 1/1995 | Lang | | 128/201.13 |
| 5,386,825 A | 2/1995 | Bates | | 128/205.27 |
| 5,390,668 A | 2/1995 | Lehman | | 128/205.27 |
| 5,398,677 A | 3/1995 | Smith | | 128/205.12 |
| 5,435,298 A | 7/1995 | Anthony | | 128/201.13 |
| 5,435,299 A | 7/1995 | Langman | | 128/201.13 |
| 5,443,723 A * | 8/1995 | Stankowski et al. | | 210/321.75 |
| 5,460,172 A | 10/1995 | Eckerbom et al. | | 128/201 |
| 5,462,048 A | 10/1995 | Lambert et al. | | 128/201.13 |
| 5,468,451 A | 11/1995 | Gedeon | | 422/58 |
| 5,474,177 A | 12/1995 | Abrams et al. | | 206/710 |
| 5,482,031 A | 1/1996 | Lambert | | 128/203.12 |
| 5,487,382 A | 1/1996 | Bezicot | | 128/207.14 |
| 5,505,768 A | 4/1996 | Altadonna | | 96/108 |
| 5,546,930 A | 8/1996 | Wikefeldt | | 128/201.13 |
| 5,555,974 A | 9/1996 | Donald et al. | | 206/1.7 |
| 5,558,088 A | 9/1996 | Smith | | 128/205.28 |
| 5,570,684 A | 11/1996 | Behr | | 128/201.13 |
| 5,577,494 A | 11/1996 | Kuypers et al. | | 128/201.13 |
| 5,590,644 A | 1/1997 | Rosenkoetter | | 128/201.13 |
| 5,592,933 A | 1/1997 | Zucchi | | 128/201.13 |
| 5,640,952 A | 6/1997 | Swann et al. | | 128/205 |
| 5,647,344 A | 7/1997 | Turnbull | | 128/201.13 |
| 5,660,173 A | 8/1997 | Newton | | 128/205 |
| 5,715,815 A | 2/1998 | Lorenzen et al. | | 128/207.14 |
| 5,738,091 A | 4/1998 | Kee et al. | | 128/205.12 |
| 5,769,268 A | 6/1998 | Kuzma et al. | | 220/780 |
| 5,829,428 A | 11/1998 | Walters et al. | | 128/200.24 |
| 5,885,455 A | 3/1999 | Graus et al. | | 210/445 |
| 5,901,705 A | 5/1999 | Leagre | | 128/207.14 |
| 5,906,201 A | 5/1999 | Nilson | | 128/203 |
| 5,931,163 A | 8/1999 | Stegmann et al. | | 128/204 |
| 5,964,223 A | 10/1999 | Baran | | 128/207.14 |
| 5,979,690 A * | 11/1999 | Hartley | | 220/266 |
| 5,992,413 A | 11/1999 | Martin, Jr. et al. | | 128/201.13 |
| 6,095,135 A | 8/2000 | Clawson et al. | | 128/201.13 |
| 6,105,756 A | 8/2000 | Fenlon | | 198/835 |
| 6,131,573 A | 10/2000 | Brown | | 128/205.27 |
| 6,202,837 B1 | 3/2001 | Mason et al. | | 206/209 |
| 6,227,200 B1 | 5/2001 | Crump et al. | | 128/207.16 |
| 6,279,576 B1 | 8/2001 | Lambert | | 128/205.28 |
| 6,363,930 B1 | 4/2002 | Clawson et al. | | 128/201.13 |
| 6,415,788 B1 | 7/2002 | Clawson et al. | | 128/201.13 |
| 6,516,798 B1 | 2/2003 | Davies | | 128/201.13 |
| 6,550,476 B1 | 4/2003 | Ryder | | 128/201.13 |
| 6,588,421 B1 | 7/2003 | Diehl et al. | | 128/201.13 |
| 6,588,425 B2 | 7/2003 | Rouns et al. | | 128/207.14 |
| 6,588,427 B1 | 7/2003 | Carlsen et al. | | 128/207.14 |
| 6,588,618 B1 * | 7/2003 | Davis | | 220/254.7 |
| D478,660 S | 8/2003 | Mault | | D24/110.1 |
| 6,629,530 B2 | 10/2003 | Cise | | 128/205.24 |
| 6,662,802 B2 | 12/2003 | Smith et al. | | 128/203.16 |
| 6,745,766 B2 | 6/2004 | Fini | | 128/204.17 |
| 6,764,243 B1 * | 7/2004 | Inuzuka et al. | | 403/50 |
| 6,769,430 B1 | 8/2004 | Carlsen et al. | | 128/201.13 |
| 6,792,946 B1 | 9/2004 | Waldo, Jr. et al. | | 128/205.12 |
| 6,951,216 B2 | 10/2005 | Heinonen | | 128/203.25 |
| 6,955,650 B2 | 10/2005 | Mault et al. | | 600/531 |
| 6,968,841 B2 | 11/2005 | Fini | | 128/204.17 |
| 6,976,488 B2 | 12/2005 | Halperin | | 128/201.13 |
| 7,055,710 B2 * | 6/2006 | King | | 215/344 |
| 7,225,945 B2 * | 6/2007 | Crider et al. | | 220/276 |
| 2002/0148846 A1 * | 10/2002 | Luburic | | 220/792 |

FOREIGN PATENT DOCUMENTS

| | | |
|---|---|---|
| GB | 2 267 840 | 12/1993 |
| GB | 2 322 568 | 9/1998 |

* cited by examiner

ASSEMBLIES FOR COUPLING TWO ELEMENTS AND COUPLED ASSEMBLIES

The present invention relates to assemblies for coupling together two elements and to coupled assemblies. More particularly, the invention relates to such assemblies which are relatively straightforward in construction, easy to manufacture and use and/or light weight, and provide couplings or joints between two elements which are very strong, can provide pressure tight seals and are resistive to being broken apart into separate elements.

Final or finished products are often made from two or more individual elements which are coupled or joined together in manufacturing the products. A great many couplings or joints have been suggested and used in the past to facilitate coupling or joining elements together. Examples of such prior art joints include conventional tongue and groove structures in which an elongated member (the tongue) is placed into a hollow space (the groove). Such tongue and groove joints often require application of large deformations of one or both elements, for example, by ultrasonic or other friction bonding techniques, and/or use of adhesives and/or solvents, for example, to provide strong couplings and/or pressure tight seals. The use of friction bonding, adhesives and/or solvents often involves an extra and expensive and potentially variable processing step. Moreover, the adhesives and/or solvents can contaminate the final product. In the prior art, to achieve high coupling strength, the tongue is interference fit into the groove, relatively heavy, thick walled structures are required to facilitate a secure interference fit. Thus, such prior art interference fit joints are relatively expensive, can add unwanted weight and/or size to the final product, and can involve undesirable permanent deflection or distortion of the parts being joined together.

Medical devices, such as respiratory gas treatment devices, other treatment devices and the like, are benefited by being light weight, small and inexpensive. Moreover, such medical devices should be sufficiently sturdy so as to be tamper resistant or even tamper proof, for example, against tampering by patients and unauthorized personnel, often in an attempt to reuse a device. In addition, medical devices can benefit from coupling systems which do not require adhesives, solvents, friction/heat bonding systems or other materials to insure secure coupling and sealing. Such adhesives, solvents, friction/heat bonding systems and/or other materials can cause detrimental reactions and/or effects in other components of the medical devices, for example, in active treatment components of such devices.

There continues to be a need for coupling or joint assemblies which address one or more of the concerns with the prior art systems.

SUMMARY OF THE INVENTION

New assemblies for coupling together two elements and coupled assemblies have been discovered. The present assemblies overcome one or more of problems or issues apparent with prior art coupling systems. For example, the present assemblies are relatively easy to manufacture, are straight forward in construction, may have elements that are inherently self-aligning to start assembly and can be assembled relatively easily, for example, manually or automatically, for example, robotically, with the application of reduced or even minimal amounts of force, and may finish assembly with no permanent functional distortion. Substantial benefits of the present assemblies include, without limitation, relatively light weight, effective and secure coupling and sealing, such as hermetic sealing, conventional polymeric materials as materials of construction, and/or thin walled construction. The present assemblies do not rely primarily on the size and/or weight of the assembly in order to maintain a secure coupling or sealing. In addition, in one embodiment, the present assemblies do not require adhesives, solvents or friction/heat bonding systems in order to provide for a secure coupling or sealing, for example, a coupling or sealing which is resistive to forces which can be generated manually, for example, by two human hands directly against the members of the coupled assemblies. Since no adhesives, solvents or other materials may need to be used, the present coupling members have a reduced risk, or even substantially no risk, of contaminating the final or finished product.

In short, the present assemblies for coupling two elements and coupled assemblies may provide one or more substantial enhancements, advantages, and/or benefits relative to prior art coupling assemblies and coupled assemblies.

In one broad aspect of the present invention, assemblies for coupling together two elements are provided and comprise a first coupling member and a second coupling member. The first coupling member is located on, for example, is a part of, a first element. The first coupling member has first and second walls defining an opening in a hollow space therebetween. The second coupling member is located on, for example, is a part of, a second element and has a body sized and adapted to be fitted into the hollow space of the first coupling member, for example, when the first and second coupling members are coupled together. The second wall of the first coupling member includes an outward step region extending toward the first wall relative to a region of the second wall closer to the opening. The outward step region is configured to deflect or bend the body of the second coupling member toward the first wall of the first coupling member as the body is passed into the hollow space, for example, when the body of the second coupling member is fitted into the hollow space, of the first coupling member.

In another broad aspect of the present invention, assemblies for coupling together two elements are provided and comprise a first coupling member and a second coupling member. The first coupling member is located on, for example, is a part of, a first element and has spaced apart first and second walls defining an opening in a hollow space therebetween. The first wall of the first coupling member includes an inward step region located away from the opening of the first coupling member and extending away from the second wall of the first coupling member relative to a region of the first wall closer to the opening. The second coupling member is located on, for example, is a part of, a second element and has a body sized and adapted to be fitted into the hollow space. The body of the second coupling member includes a first surface having an outward step portion positioned to be located in proximity to the inward step region of the first wall of the first coupling member when the body is fitted into the hollow space of the first coupling member. The body of the second coupling member further includes a second surface substantially opposing the first surface of the body.

The second wall of the first coupling member includes an outward step region further away from the opening than the inward step region of the first wall of the first coupling member and extending toward the first wall relative to a region of the second wall closer to the opening. Alternately, the second surface of the second coupling member includes an outwardly projecting portion positioned more distally on the body of the second coupling member relative to the outward step portion of the body. The outwardly projecting portion extends away from the first surface of the second coupling member relative to a more proximal portion of the second surface. The second surface of the body of the second coupling member is configured to be in contact with the second wall of the first coupling member at the outward step region or the outwardly projecting portion to deflect the body when the body is fitted into the hollow space of the first coupling member.

In the event the second wall of the first coupling member includes an outward step region, as described herein, the second surface of the body of the second coupling member may be configured to be in contact with the outward step region along substantially a single contact line when the body is fitted into the hollow space of the first coupling member. In the event the second surface of the body of the second coupling member includes an outwardly projecting portion, as described herein, the second wall of the first coupling member may be configured to be in contact with the outwardly projecting portion along substantially a single contact line when the body is fitted into the hollow space.

The outward step region of the first coupling member or the outwardly projecting portion of the body of the second coupling member may be configured and be effective to deflect or bend the body of the second coupling member toward the first wall of the first coupling member as the second coupling member is passed into the hollow space, for example, when the body of the second coupling member is fitted into the hollow space, of the first coupling member.

In a further broad aspect of the invention, assemblies for coupling together two elements are provided. Such assemblies comprise a first element having a first wall defining an inward step region and a spaced apart second wall; and a second element having a body including a first surface having an outward step portion positioned to be located in proximity to the inward step region when the first and second elements are coupled together. In one embodiment, the second wall of the first element includes an outward step region positioned and effective, when the first and second elements are coupled together, to be in contact with and deflect or bend the body of the second element toward the inward step region of the first element and form a seal between the first and second elements. In another embodiment, the body of the second element includes a second surface having an outwardly projecting portion positioned and effective, when the first and second elements are coupled together to be in contact with the second wall of the first element to thereby deflect or bend the body toward the inward step region of the first element and form a seal between the first and second elements.

In a very useful embodiment, the first and second elements are structured so that when the first and second elements are coupled together and an increased internal fluid pressure is generated tending to open the coupling of the first and second elements, the increased internal fluid pressure causes the seal between the first and second elements to be effective against increased fluid pressures relative to a seal between the first and second elements without the increased fluid pressure.

In one embodiment, the first coupling member and the second coupling member are configured so that such coupling members can be assembled together with substantially minimal or minimum resistance until the second surface of the body of the second coupling member comes into resisting contact with the second wall of the first coupling member at the outward step region or the outwardly projecting portion. This feature greatly adds to the ease in which the first and second coupling members are assembled or coupled together.

As used herein, the term "resisting contact" means that at the area at which resisting contact occurs substantially increased force, for example, at least about 150% or at least about 200% or at least about 300% or at least about 500% or more of force, is required to move the second coupling member further into the hollow space relative to the amount of force, for example, the maximum amount of force, required to move the body of the second coupling member into the hollow space of the first coupling member before reaching the area at which resisting contact occurs.

In a useful embodiment, the first and second coupling members are configured so that the body of the second coupling member has a distal end which extends into the hollow space to a distance when the body is fitted into the hollow space. Advantageously, the second surface of the body of the second coupling member comes into resisting contact with the second wall of the first coupling member at the outward step region or the outwardly projecting portion when the distal end of the body of the second coupling member is in the hollow space to an extent of at least about 65% or at least about 75% or at least about 85% of the distance. This feature also allows for convenient and relatively easy assembly or coupling of the first and second coupling members. In particular, the body of the second coupling member is allowed into the hollow space of the first coupling member for a relatively long distance or long travel before substantial resistance is encountered. This allows the two coupling members to be very easily placed in position so that when force is exerted on the first and/or second coupling members the fit between the first and second coupling members is accomplished quickly and very effectively.

In one embodiment, the first and second coupling members are configured so that the first and second coupling members form a seal, for example, a hermetic seal, such as a seal resulting from the first and second coupling members being in sealing contact with each other.

In one useful embodiment, the first and second coupling members may be configured so that (1) the outward step region of the second wall of the first coupling member is in sealing contact with, for example, is embedded, such as slightly embedded, in, the second surface of the body of the second coupling member when the body is fitted into the hollow space of the first coupling member, for example, so that the second wall extends into the body a distance in a range of about 0.1% or less to about 1% or about 5% or more of the thickness of the body at the embedded area, or (2) the outwardly projecting portion is in sealing contact with, for example, is embedded, for example, slightly embedded, in, the second wall of the first coupling member when the body of the second coupling member is fitted into the hollow space of the first coupling member, for example, so that the outwardly projecting portion extends into the first coupling member a distance in a range of about 0.1% or less to about 1% or about 5% or more of the thickness of the first coupling member at the embedded area. Such sealing contact, for example, embedding, such as along a narrow line or near line or substantially single line of contact, facilitates a strong, consistent, and advantageously sealing coupling between the first and second coupling members, for example, with minimum load and deformation on the coupled assembly.

In one embodiment, with the first and second coupling members fitted together, such as with the body of the second coupling member fitted into the hollow space of the first coupling member, both the first and second coupling members yield to a sufficient extent to provide a seal, for example, a hermetic seal, which seal may be effective to hold against pressures or forces encountered in use of the coupled assembly and/or which may be effective at a pressure or a force which is reduced relative to a yield pressure or force sufficient to cause at least one of the first coupling member and the second coupling member to destructively yield.

In this context, the term "destructively yield" refers to a coupling member which has had a sufficient force or pressure applied to it that the coupling member has been permanently structurally compromised so that it can no longer be employed in a coupled assembly in accordance with the present invention. The embedding or slight embedding described herein as being useful in accordance with the present invention can be considered as resulting from the non-destructive yielding of the first coupling member and/or the second coupling member.

In practice, the "substantially single contact line" between the first and second coupling members, described elsewhere herein, has a finite width. The contacting of second wall (from the first coupling member) and the second surface (from the second coupling member) in accordance with the present invention may cause a small amount of yielding. Therefore, at at least a portion of this area of contact between the second wall of the first coupling member and the second surface of the body of the second coupling member at the outward step region or the outwardly projecting portion, the yield point or yield stress of the materials may be exceeded. However, the design and construction (including, without limitation, materials of construction) of the first and second coupling members may be selected so that the width of the contact area or the "substantially single contact line" is kept small to reduce, or even substantially minimize, the area of deformation and/or yield. The yield that occurs in this context, in accordance with the present invention, is not destructive yield as it relates to the first coupling member or the second coupling member. Of course, when it is desired to form a seal, for example, a hermetic seal, between the first and second coupling members, this contact force or pressure, for example, described as pounds per square inch of pressure on the substantially single contact line, is larger than the fluid pressure to be sealed against in providing the desired seal.

The sealing contact or embedding described herein may be considered one form of interference fitting. Such sealing contact or embedding is advantageous in providing seals, for example, hermetic seals, between first and second coupling members in accordance with the present invention. However, it is to be understood that sealing contact interference may not be the only, or even the primary, source of holding or coupling the first and second coupling members assembled together with the body of the second coupling member fitted into the hollow space defined by the first coupling member.

The first and second coupling members may be configured so that an attempt to remove the body from the hollow space after the body is fitted into the hollow space causes one or more visually identifiable alterations in at least one of the first and second coupling members. This feature of the present invention is useful in allowing one to determine whether or not the coupling between the first and second coupling members has been tampered with or whether an attempted tampering of such coupling has occurred. In certain situations, for example, and without limitation, with medical devices using the first and second coupling members, even an attempt to tamper with the coupling of the first and second coupling members is sufficient grounds for changing the medical device, for example, because of possible outside contamination caused by tampering or even an attempt to tamper with the coupling, for example, in an attempt to reuse a disposable device.

In one embodiment, the first coupling member or the second coupling member further comprises at least one retention member positioned and structured to retain a further component in place relative to the first or second coupling member prior to the body of the second coupling member being fitted into the hollow space of the first coupling member. This feature facilitates ease of manufacture of the coupled assembly. The retention member or members are particularly useful when another component, for example a filter, a fibrous member, a woven member, a screen or the like, is placed between the first and second elements. The retention member or members advantageously are effective in causing the other component to remain in place relative to the first and/or second coupling members so that when the coupling members are coupled together, the other component is in the correct position in the assembled device. In one embodiment, the at least one retention member comprises a plurality of pointed projections extending between the first and second coupling members when the body is fitted into the hollow space. The at least one retention member may be a part of the first coupling member or the second coupling member.

The second coupling member advantageously has sufficient flexibility to be deflected by the outward step region or the outwardly projecting portion. Materials of construction which provide for such flexibility are useful for producing the first and second coupling members, and in particular the second coupling member.

In one embodiment, at least one of the first and second coupling members, preferably both of the first and second coupling members comprise a polymeric material, for example, selected from substantially inert polymeric materials, substantially non-reactive polymeric materials and the like. The polymeric material may be a thermoplastic polymeric material. Examples of useful polymeric materials which may be used as materials of construction for the first and/or second coupling members include, without limitation, polyolefins, such as polyethylene, polypropylene, ethylene/propylene copolymers, polystyrene and the like and mixtures thereof; acrylic polymers, such as polyacrylates, polymethacrylates and the like and mixtures thereof; other polymeric materials suitable and sized to provide the desired flexibility and/or one or more other properties desired in the present first and second coupling members, and the like and mixtures thereof; and combinations thereof.

In one embodiment, the inward step region of the first wall of the first coupling member forms at a substantially sharp angle with the region of the first wall closer to the opening; and the outward step portion of the first surface of the body of the second coupling member forms at a substantially sharp angle with a portion of the first surface closer to the opening. Each of the angles may be independently in a range of about 30° to about 85°. In one very useful embodiment, the outward step portion is in closer proximity to, and may be in contact with, the inward step region of the first wall of the first coupling member when the body of the second coupling member is fitted into the hollow space of the first coupling member relative to an identical assembly with no outward step region and no outwardly projecting portion. The ability of the outward step region or the outwardly projecting portion to be effective in deflecting the body toward the first wall is highly advantageous, for example, in combination with one or more other features of the present assemblies, to provide the desirably strong coupling and/or pressure tight sealing of the first and second coupling members in accordance with the present invention.

In one embodiment, the first and second coupling members, when fitted together, are more resistant to being separated relative to an identical assembly with no outward step region on the second wall of the first coupling member and no outwardly projecting portion on the second surface of the body of the second coupling member.

In one useful embodiment, the present assembly is structured so that the body of the second coupling member cannot be non-destructively removed from the hollow space of the first coupling member, for example, manually by human hands.

The first coupling member may have a closed end wall substantially opposing the opening.

In one very useful embodiment, the first and second coupling members extend along or near peripheries of first and second elements, respectively. The first and second coupling members may be generally annular and/or may be substantially continuous, and extend along or around or near peripheries, for example, curved peripheries of first and second elements, respectively. For example, the first and second coupling members may extend completely or substantially completely alone or around or near peripheries of first and second elements, respectively.

The present assemblies may comprise the first and second elements, for example when the body of the second coupling member is fitted into the hollow space of the first coupling member. When the body is fitted into the hollow space, a hermetic seal may be formed which is effective against fluid pressures less than the yield stress generated in the material of construction of one or both of the first and second coupling members.

The present assemblies may be portions of a wide variety of apparatus in which it is desired to couple and/or seal first and second elements. Examples, without limitation, of such apparatus include those selected from containers, such as hazardous material containers, medical waste containers and the like, medical devices, filters, separators, heat exchangers, moisture exchangers, heat generators, moisture generators, gas absorbers, humidifier chambers, gas-liquid manifolds, valved manifolds, check valves, nebulizers, metered dose inhalers, sensor housings, water traps and the like. In one very useful embodiment, the first and second elements are portions of an apparatus for treating respiratory gases in which the respiratory gases are treated to provide at least one of filtration, heat exchange, moisture exchange, heat generation, moisture generation and the like and combinations thereof.

Each and every feature described herein, and each and every combination of two or more of such features, is included within the scope of the present invention provided that the features included in such a combination are not mutually inconsistent.

These and other aspects and advantages of the present invention are apparent in the following detailed description and claims particularly when considered in combination with the accompanying drawings in which like parts bear like reference numerals.

DETAILED DESCRIPTION OF THE DRAWINGS

Figure 1:
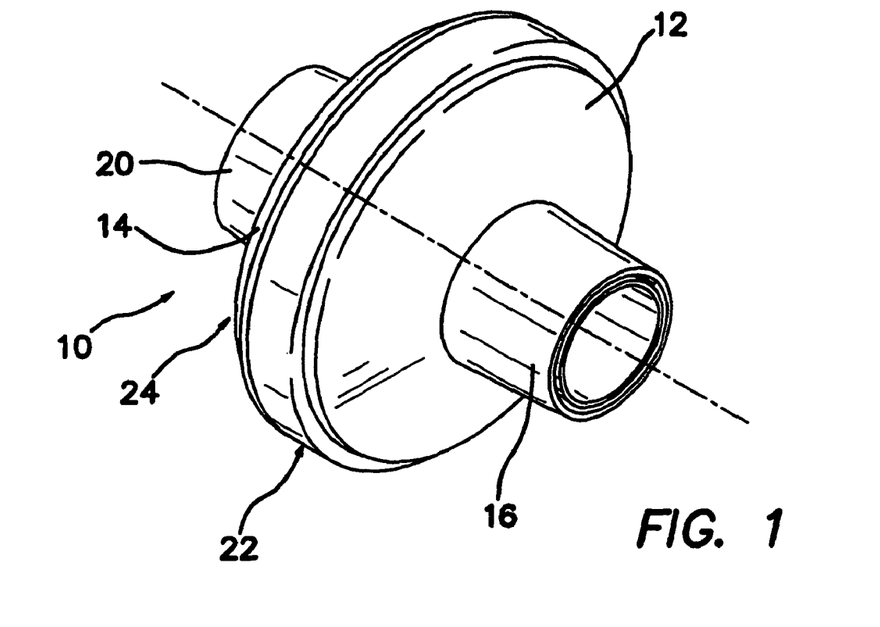
FIG. 1 is a perspective view of an apparatus including two elements coupled together which includes an embodiment of an assembly in accordance with the present invention.

With reference to FIG. 1, a housing 10 is shown which includes a first housing element 12 joined or coupled to a second housing element 14. Although the housing 10 is described herein as being a respiratory gas filter, it is to be understood that the housing 10, with appropriate and conventional modifications, can be any of many structures, for example, as described elsewhere herein, including two elements that are to be coupled together. In other words, any two elements which are to be or are coupled together using coupling assemblies as set forth herein are included within the scope of the present invention. The specific apparatus disclosed herein are for illustrative purposes and are not intended to limit the invention.

Figure 2:
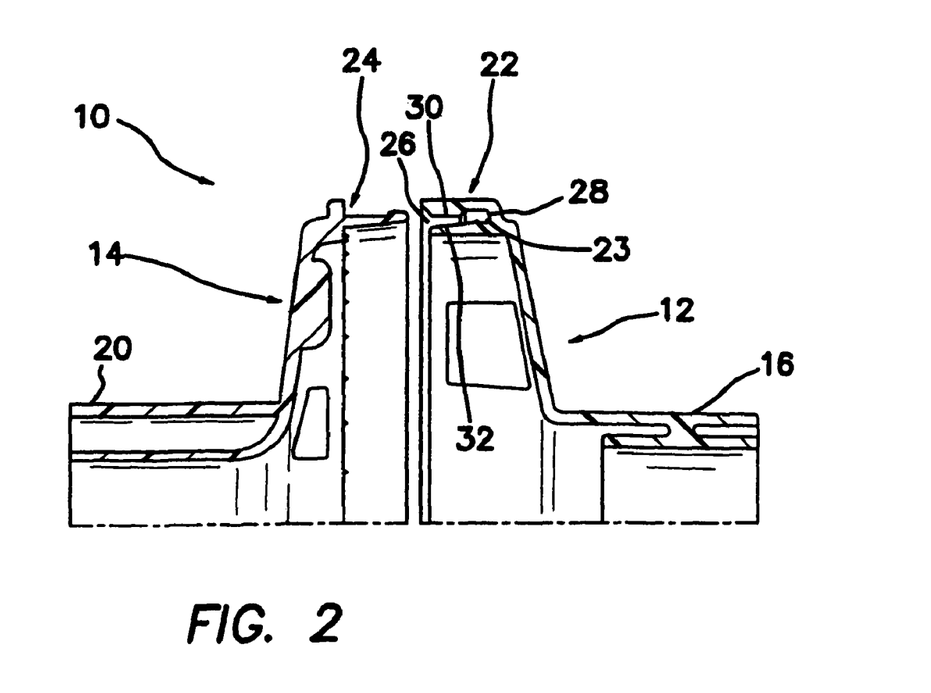
FIG. 2 is a partial cross-sectional view of the two elements of the apparatus of FIG. 1 separated from each other for illustrative purposes.
Figure 3:
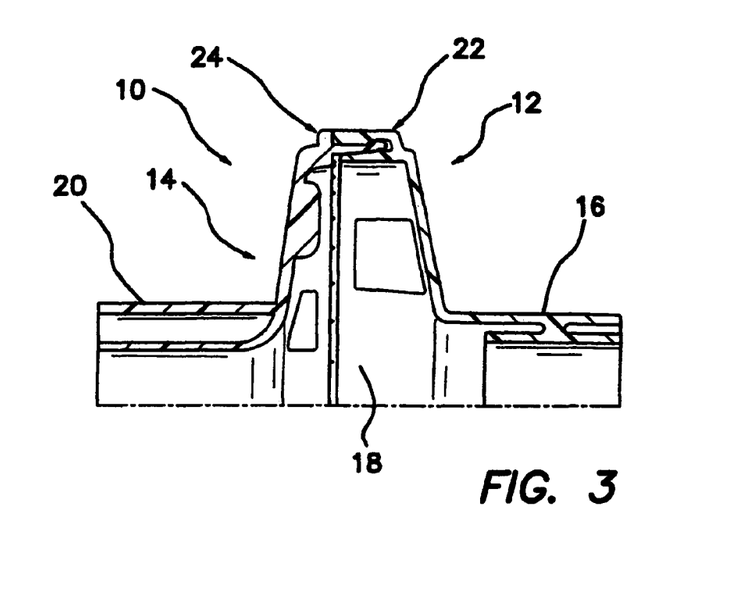
FIG. 3 is a partial cross-sectional view of the two elements of the apparatus of FIG. 1 coupled together.

Referring now to FIGS. 1, 2 and 3, housing 10 includes a first tubular conduit 16 which is in fluid communication with the interior 18 of the housing 10, and a second tubular conduit 20 which is in, fluid communication with the interior 18. First tubular conduit 16 is a part of first housing element 12, and second tubular conduit 20 is a part of second housing element 14. The housing elements 12 and 14 can be made of conventional materials, such as polymeric materials, for example, and without limitation, polypropylene, using conventional and well known techniques, for example, molding techniques.

Figure 4:
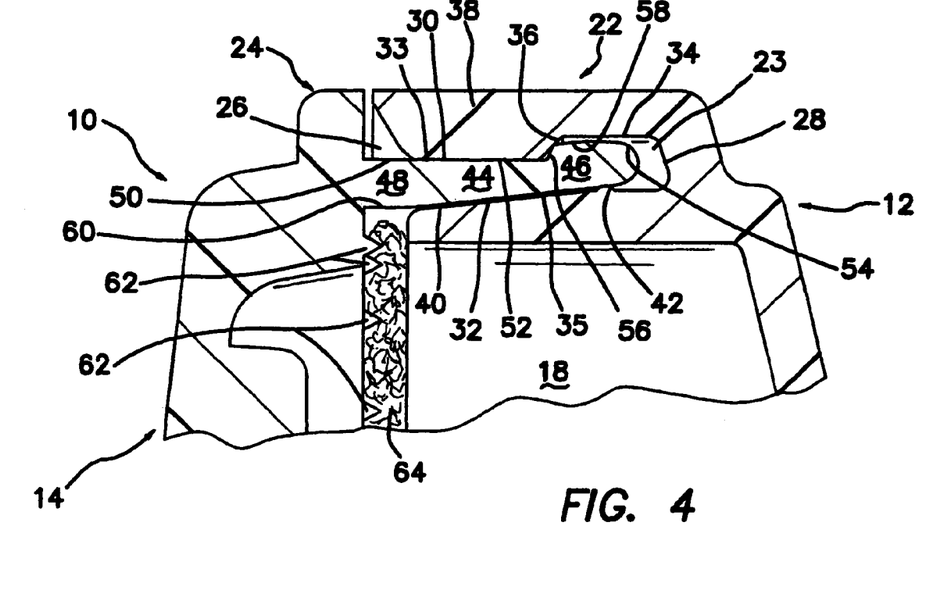
FIG. 4 is a close up view of a portion of FIG. 3 showing the coupling members of the elements in detail.

As shown in FIGS. 1, 3 and 4, first and second housing elements 12 and 14 are coupled together, whereas in FIG. 2 the housing elements are shown separated. However, in each of these drawings the first housing element 12 includes a first coupling member 22 located at or near an outer periphery of the housing 10 and the second housing element 14 includes a second coupling member 24 located at or near an outer periphery of the housing 10. It is important to understand that first and second coupling members 22 and 24 are annular and continuous and extend along or near the periphery of first and second housing elements 12 and 14, respectively. Although the housing 12 has a general circular periphery, it should be understood that the present invention is useful with housings and housing elements which have any suitable shapes, for example, ovoid, ellipsoidal, triangular, square, rectangular, polygonal and the like, as long as smooth suitably large radiused transitions are present between planar sides.

First coupling member 22 includes a hollow space 23 defined by an opening 26 and an opposing closed end 28, and first and second walls 30 and 32. First wall 30 includes a proximal region 33 which is relatively near the opening 26 and the second wall 32. First wall 30 also includes a distal region 34 which is relatively far from the opening 26 and the second wall 32.

An angled region 36 is located between proximal region 33 and distal region 34. Angled region 36 extends at a substantially sharp angle of about 45° from each of proximal and distal regions 33 and 34. The angled region 36 can be considered an inward step region because angled region 36 extends from proximal region 33 further "in" first leg 38 of first coupling member 12 to distal region 34. Both proximal region 33 and distal region 34, as well as angled region 36, of first wall 30 are substantially planar in section view, as shown in FIG. 4, and extend continuously around and near the periphery of housing 10.

Except as otherwise described herein, second wall 32 is substantially planar in section view, as shown in FIG. 4, and extend continuously around and near the periphery of housing 10. In the event the first wall 30 and/or second wall 32 or one or more portions thereof are tapered or angled, such first wall and/or second wall and one or more portions thereof have substantially conical configurations around and near the periphery of housing 10. The proximal portion 40 of the second wall is oriented from the opening 26 back toward the back wall 28 at a relatively shallow angle, for example, less than about 10°, such as in a range of about 1° to about 5°, relative to the proximal region 33 of the first wall 30.

In the embodiment shown in FIGS. 1-4, second wall 32 includes a distal region 35 which, in turn, includes only one rounded region 42 extending outward further into hollow space 23 relative to proximal region 40 of second wall 32. As shown in FIG. 4, second wall 32 includes only one outwardly extending region, that is outwardly extending region 42. Rounded outwardly extending region 42, like angled region 36, is annular and continuous, that is continuous around the first coupling member 22 and first housing element 12. As shown in the FIG. 4, rounded region 42 is located entirely further away from opening 26 than angled region 36.

Second housing element 14 includes an elongate body 44 which, as described herein, is structured to be fitted into hollow space 23. Body 44 includes a distal portion 46 which is somewhat larger or more thick than the proximal portion 48 of the body 44.

Body 44 includes a first surface 50 extending along the length of body 44. The proximal portion 52 of first surface 50 is substantially planar in section view, as shown in FIG. 4, and extends continuously and completely around and near the periphery of housing 10. The distal portion 54 of the first surface 50 has a generally rounded configuration. Intermediate between the proximal portion 52 and the distal portion 54, the first surface 50 includes first angled portion 56 and second angled portion 58.

First angled portion 56 extends outwardly away from second surface 60 of body 44, which extends along the length of body 44, as shown in FIG. 4. First angled portion 56 extends from proximal portion 52 to second angled portion 58, while second angled portion 58 extends from first angled portion 56 to distal portion 54 of first surface 50. The first angled portion 56 or the combination of the first and second angled portions 56 and 58 may be considered to be an outward step portion.

As shown in FIG. 4, angled region 36 is positioned at an angle, such as an acute angle, relative to the proximal region of the first wall 30. The first angled portion 56 is positioned at another angle, such as an acute angle, relative to the proximal portion 52 of the first surface 50. The second angled portion 58 is positioned at a further angle, such as an acute angle, relative to the proximal portion 52 of the first surface 50. Each of the angle, the other angle and the further angle is different in size, for example, extends over a different number of degrees, relative to the other two angles. In the embodiment of FIG. 4, the acute angle at which angled region 36 is positioned is larger than the other acute angle at which first angled portion 56 is positioned, and the other acute angle at which the first angled portion 56 is positioned is larger than the further acute angle at which second angled portion 58 is positioned.

As shown in FIG. 4, first and second angled portions 56 and 58 are positioned to be located in proximity to, for example, in contact with, the angled region 36 of first wall 30 of first coupling member 22 with the first and second coupling members 22 and 24 are fitted together.

In the embodiment shown in FIGS. 1-4, the second surface 60 of body 44 is substantially planar in section view, as shown in FIG. 4, and extends continuously around and near the periphery of housing 10. Second surface 60 is oriented from the proximal portion 46 toward the distal portion 48 of the body 44 at a relatively shallow angle, for example, less than about 10°, such as in a range of about 1° to about 5°, relative to the proximal portion 52 of the first surface 50.

In addition, as best shown in FIG. 4, second coupling member 24 includes a plurality of relatively sharp projections 62 which extend around the second coupling member in proximity to the body 44. These projections 62 are formed, e.g., molded, as an integral part of the second coupling member 24 or second housing element 14. Such projections 62 are very useful in at least assisting in retaining or holding a component, such as filter element 64 as shown in FIG. 4, to second coupling member 24 or second housing element 14 during assembly of the coupled housing 10. Thus, during assembly, filter element 64 is placed in second coupling member 24 so that the filter element 64 comes in contact with and is held in place by the projections 62. In addition, filter element 64 may be constrained by a slight press fit inside second surface 60 which constrains the filter to be round on its outside diameter and retains filter element 64 in position by friction during assembly. With the filter element 64 thus secured, first and second coupling members 22 and 24 can easily be coupled together, as described elsewhere herein, to form a finished product with the filter element 64 in its proper location.

First and second housing elements 12 and 14 can be coupled together as follows. After the space between first and second housing elements 12 and 14 has been filled, or partially filled with the desired component or components, such as filter element 64, the two housing elements 12 and 14 are brought together, starting from the position shown in FIG. 2.

The first and second housing elements 12 and 14 are moved together until resisting contact between the body 44 and the first and second walls 30 and 32 is encountered. Up until the time that such resisting contact is encountered, moving the first and second housing elements 12 and 14 together can be accomplished very easily, for example, by the application of substantially minimal manual force. Such substantially minimal manual force is effective to move the rearward portion 54 of first surface 50 more than about 75%, for example, about 85%, of the total distance it is to travel in the hollow space 23 so that the first and second coupling members 22 and 24 are fitted together. This relatively long distance of travel before additional resisting contact from rounded region 42 is encountered is useful in enhancing the ease in which the coupling members 22 and 24 and housing elements 12 and 14 can be initially positioned prior to actually finishing the fitting of the coupling members together. This feature is useful in reducing production of off-spec product and/or product which must be scrapped.

Once resisting contact is encountered from rounded region 42, increased amounts of force are applied to overcome this resistance. Often the increased amount of force can still be generated manually, that is generated directly by the hands of a human being. Such increased amount of force can be at least about 150% or about 200% or about 300% or about 400% or about 500% or more of the force required before such resisting contact is encountered.

By applying the additional amount of force to one or both of the first and second housing elements 12 and 14, the resisting contact is overcome and the first and second coupling members 22 and 24 are fitted together, as shown in FIG. 4.

Once the coupling elements 22 and 24 are thus fitted together, the joint formed is strong and highly resistive to being broken or compromised. For example, and without limitation, the formed joint is advantageously sufficiently strong so that it cannot be broken by a force generated by human hands applied directly to the joined housing elements 12 and 14 without destroying one or both of the coupling members 22 and 24.

Without wishing to limit the invention to any particular theory of operation, it is believed that as the body 44 is made to travel distally in the hollow space 23, the angled portion 56 of the first surface 50 of the body 44 passes rearward or distal of the angled region 36 of the first wall 30 of the first coupling member 22. In addition, it is believed that the second surface 60 of body 44 comes into contact with the rounded region of second wall 32, which causes the body 44, and in particular the rearward or distal portion 46 of body 44, to deflect away from second wall 32 and toward first wall 30, and in particular toward rearward or distal region 34 and angled region 36 of first wall 30. First and second angled portions 56 and 58 of first surface 50 of body 44 come into close proximity to, or contact with angled region 36. As shown in FIG. 4, the body 44 is not in contact with the first wall 30 distal of the angled region and is not in contact with the closed end wall 28, which extends from the first wall 30 to the second wall 32. When the first and second coupling members 22 and 24 are fitted together, it is believed that body 44 remains in contact with rounded region 42 along substantially a single very narrow line of contact. The rounded region 42 may become slightly embedded in the body 44 to act in further securing fitting of coupling members 22 and 24 together, for example, to form a hermetic seal between the coupling members.

Although the housing elements 12 and 14 can be fitted together manually, they can also be fitted together semi-automatically, that is with the use of both direct human intervention or manipulation and automatic means, or automatically, that is without direct human intervention or manipulation, for example, robotically and the like.

Coupling members 22 and 24 are made, for example, molded, of a polymeric material, for example, a thermoplastic polymeric material, such as a polyolefinic material, a polycarbonate material, an acrylic material, and the like and combinations thereof. Such polymeric materials advantageously have a degree of flexibility sufficient to allow for rapid assembly of the first and second coupling members 22 and 24 and the deflection of the body 44 toward the first wall 30, as described herein. Such coupling members 22 and 24, and the housing elements 12 and 14 have sufficient strength so that the coupling members remain assembled after the second coupling member 24 is fitted into the first coupling member 22, as described herein.

The strength of the coupling and sealing of first and second coupling members 22 and 24 is not entirely due to the strength of the as molded walls and surfaces of the first and second coupling members. The structure of the first and second coupling members 22 and 24, for example, the structure of first and second walls 30 and 32, body 44 and first and second surfaces 50 and 60, as described herein, as well as the ability of the body 44 to be deflected causing increased pressure on angled region 36 and angled portion 56 are substantial factors in providing increased coupling and/or sealing strength, for example, coupling strength sufficient so as not to be non-destructively manually decoupled, as described herein.

The structure of the first and second elements 12 and 14 and first and second coupling members 22 and 24 is such that when the first and second elements are coupled together a seal is advantageously formed between the first and second members. This seal is effective against an increased internal fluid pressure, for example, such pressure which tends to open the coupling of the first and second elements, relative to a seal between the first and second elements without the increased fluid pressure. In other words, the present assemblies are structured so that an increase in the internal fluid pressure results in an increase in the strength of the seal between the first and second elements.

Without wishing to limit the invention to any particular theory of operation, it is believed that as the internal fluid pressure within the hollow space defined by the first and second elements 12 and 14 increases, the second wall 32 of the first coupling member 22 moves radially outwardly. This movement causes the body 44 of the second coupling member 24 to more securely or more robustly contact the rounded region 44, which may be considered a seal rib, of the first coupling member 22, resulting in an enhanced seal between the body 44 and the seal rib, which enhanced seal is effective against increased internal fluid pressure.

In the event that one or both of the angled portions 56 and 58 of body 44 are in contact with angled region 36 when first and second coupling members 22 and 24 are fitted together, any attempt to separate the coupling members can result in creating marks or blemishes on the angled region 36. Thus, although the coupling of first and second coupling members 22 and 24 remains secure and intact, by looking at the housing 10, and in particular at the angled region 36 one can identify marks or blemishes and determine that an attempt to decouple the coupled members 22 and 24 has occurred. As noted previously, in certain cases even an attempt to break the joint between housing elements 12 and 14 may result in replacing the housing 10. Even if no replacement is called for, having evidence that an attempt has been made to break the joint between coupling members 22 and 24 can result in taking extra precautions to avoid further such attempts in the future.

Because the strength of the coupling of the first and second coupling members 22 and 24 does not rely only on the strength of thick walled materials of construction or on the weight or size of such members, it is possible to use coupling members which are relatively small, for example, relatively thin-walled, and/or made of lightweight materials. This feature makes the present assemblies advantageously useful in applications, for example and without limitation, in medical applications and the like, where physically small and/or lightweight coupling assemblies and systems are desirable and/or can be beneficially used.

An alternate embodiment of the present invention is illustrated with reference to FIGS. 5-7. Except as expressly described herein, the alternate housing, shown as 110, is structured and functions similarly to housing 10. Components of alternate housing 110 which correspond to components of housing 10 are provided with the same reference numeral increased by 100.

Figure 5:
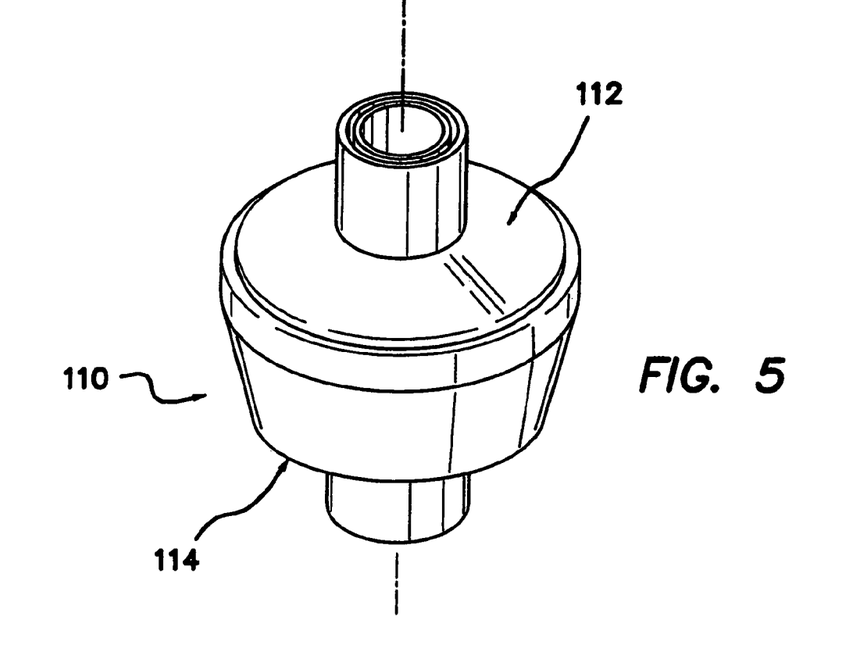
FIG. 5 is a perspective view of an apparatus for heat and moisture exchange with respiratory gases, which apparatus includes two elements coupled together and includes another embodiment of an assembly in accordance with the present invention.
Figure 6:
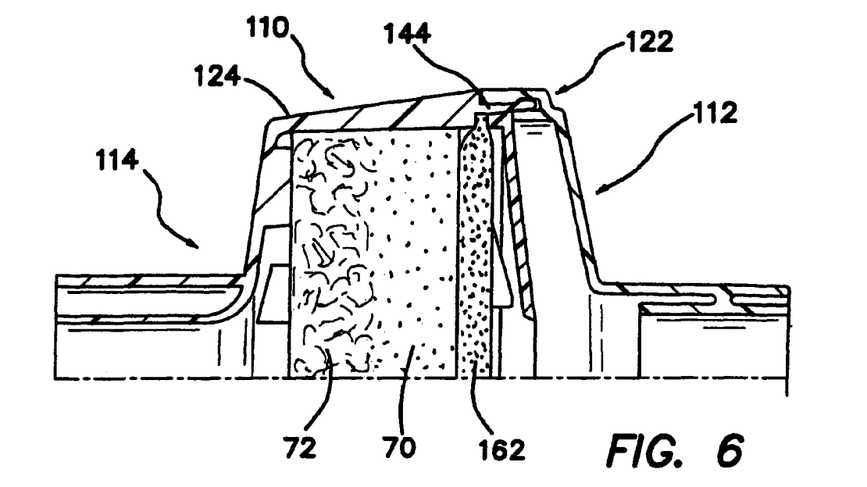
FIG. 6 is a partial cross-sectional view of the two elements of the apparatus of FIG. 5 coupled together.

With reference now to FIGS. 5 and 6, housing 110 is for a heat and moisture exchange apparatus for respiratory gasses. Again, although housing 110 is described herein as being for a respiratory gas heat and moisture exchanger, it should be understood that the housing 110, with appropriate and conventional modifications, can be any of many structures including two elements that are coupled together.

Housing 110 includes a first housing element 112 including a first coupling member 122 joined to a second housing element 114 including a second coupling member 124.

Figure 7:
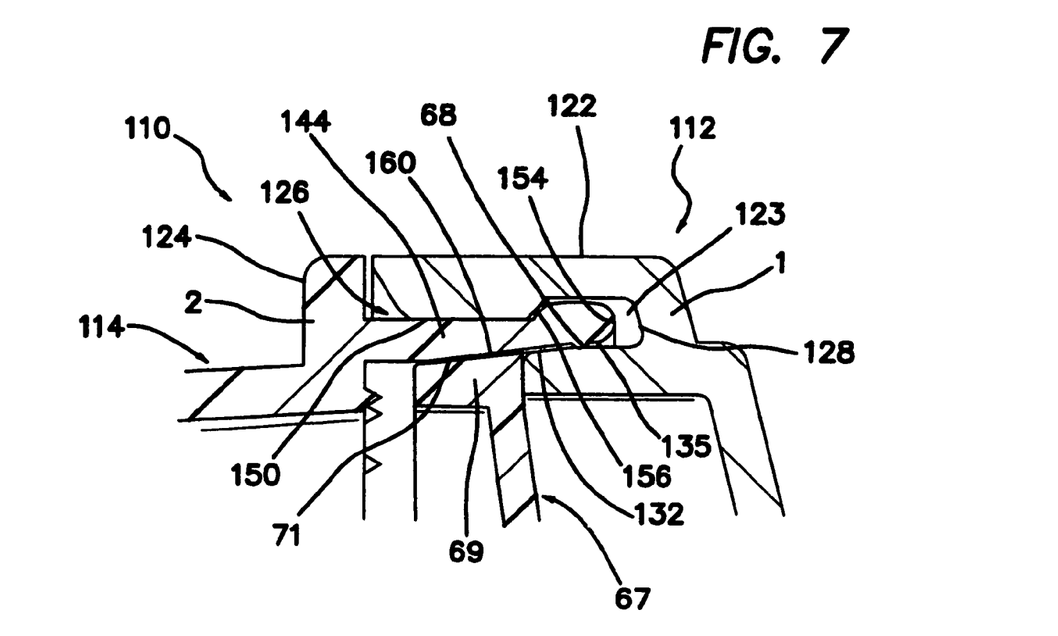
FIG. 7 is a close up view of a portion of FIG. 6 showing the coupling members of the elements in detail.

As shown in FIG. 7, one primary difference between housing 10 and alternate housing 110 involves the structure of second wall 132 of first coupling member 122 and the structure of second surface 160 of second coupling member 124. A liquid baffle 67 is included within housing 110. Liquid baffle 67 is used to deflect liquid entering housing 110 with respiratory gases from a patient. Baffle 67 includes a peripheral flange 69 which extends around housing 110 near its periphery. Flange 69 includes an outer wall 71. Flange 69 is sized and configured to be positioned in contact with first coupling member 122 and to provide the proximal region of the second wall 132. In other words, outer wall 71 of flange 69 is positioned to provide the proximal region of the second wall 132 of first coupling member 122. To this extent at least, flange 69, and in particular, outer wall 71, may be considered to be part of first coupling member 122.

Second wall 132, including proximal region 71 and distal region 135, extends from opening 126 to closed end 128. Second wall 132 does not have a rounded region extending outwardly further into hollow space 123 as does second wall 32 of first coupling member 22. In addition, as shown in FIG. 7, second surface 160 of body 144 of second coupling member 124 includes only one outwardly projecting portion, that is outwardly projecting portion 68 which is located entirely further distally on body 144 relative to angled portion 156.

First and second housing elements 112 and 114 and baffle 67 can be coupled together as follows. After the space between first and second housing elements 112 and 114 has been filled or at least partially filled with the desired component or components, such as filter element 162 moisture generating material 70 and fibrous material 72 (as shown in FIG. 6), the two housing elements and the baffle 67 are fitted together, as shown in FIG. 7. Thus, the separate first and second housing elements 112 and 114 and baffle 67 are moved together with body 144 passing into hollow space 123 until resisting contact between the body 144 and the first and second walls 130 and 132 of first coupling member 112 is encountered. Up until the time that such resisting contact is encountered, moving the first and second housing elements 112 and 114 together can be accomplished very easily, for example, with application of substantially minimum or minimal manual force. Such substantially minimum manual force is effective to move the distal portion 154 of first surface 150 more than 75%, for example, about 85%, of the total distance it is to travel in the hollow space 123 so that the first and second coupling members 122 and 124 are fitted together.

Once resisting contact is encountered, increased amounts of force are applied to overcome this resistance. Often the increased amounts of force can still be generated manually, that is generated directly by the hands of a human being.

By applying the additional amounts of force to one or both of the first and second housing elements 112 and 114, the resisting contact is overcome and the coupling members 122 and 124 are fitted together, as shown in FIG. 7. Once the coupling members 122 and 124 are fitted together, the joint formed is strong and highly resistive to being broken or compromised. For example, and without limitation, the formed joint is advantageously sufficiently strong so that it cannot be broken by a force generated by human hands applied directly to the joined housing elements 112 and 114 without destroying one or more of the coupling members 122 and 124.

The combination of the outwardly projecting portion 68 and the second wall 132 is effective to deflect the body 144 toward the first wall 130 so that the body 144 comes in close proximity to or contact with angled portion 136. As shown in FIG. 7, the body 144 is not in contact with the first wall 130 distal of the angled region and is not in contact with the closed end wall 128, which extends from the first wall 130 to the second wall 132. The outwardly projection portion 68 of the second surface 160 of the body 144 of second coupling member 124 remains in contact with the second wall 132 of the first coupling member 122 while the first coupling member 122 and the second coupling member 124 remain fitted together. Such contact is along a substantially single very narrow line of contact. The outwardly projecting portion 68 may become slightly embedded in the first coupling member 122 through the first wall 132 of the first coupling member 122. Such slight embedding is effective in further securing fitting of the coupling members 122 and 124 together, for example, to form a hermetic seal between the coupling members.

In effect, the combination of outwardly extending portion 68 and second wall 132 function substantially similarly to the combination of rounded region 42 and second surface 60 to provide a highly effective coupling and sealing of the first and second coupling members 122 and 124. Additional specific applications for the joints disclosed in the present invention are shown with regard to FIGS. 8 and 9. It should be noted that the coupling members, that is the first and second coupling members, described with reference to FIGS. 8 and 9 can either correspond to coupling members 22 and 24 or alternate coupling members 122 and 124. When referring to FIGS. 8 and 9, such coupling members are identified as coupling members 222 and 224. However, it should be noted that each pair of coupling members is structured and functions similarly to the corresponding pair of coupling members referred to in FIGS. 1 to 7.

Figure 8:
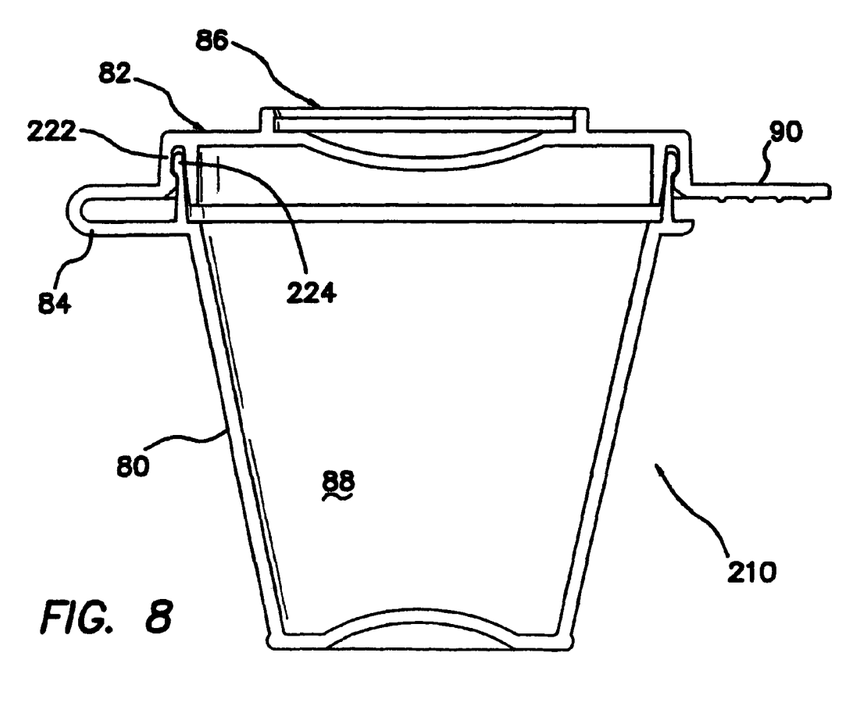
FIG. 8 is a cross-sectional view of a container including two elements coupled together which includes an embodiment of an assembly in accordance with the present invention.

With regard to FIG. 8, a medical sample container 210 for example, made of a softer polymeric material, such as polyethylene or polypropylene is shown which includes a container portion 80 and a cover portion 82. The cover portion and container portion 80 are linked together by flexible connecting element 84. In addition, a first coupling member 222 and second coupling member 224 are coupled together to form a sealed container. The cover portion can include a large gap between the elements allowing a tool to be inserted to facilitate opening the hermetically sealed sample container in a laboratory with the proper tool.

One additional feature of the container 210 is a finger tab 90 which extends radially outwardly from the first coupling member 222. Generally, upward force can be applied to tab 90, for example, manual force, to release the second coupling member from the first coupling member in removing the cover portion 82 from on top of the container portion. This opening can be done, for example, when it is desired to obtain access to the sample within interior 88.

Figure 9:
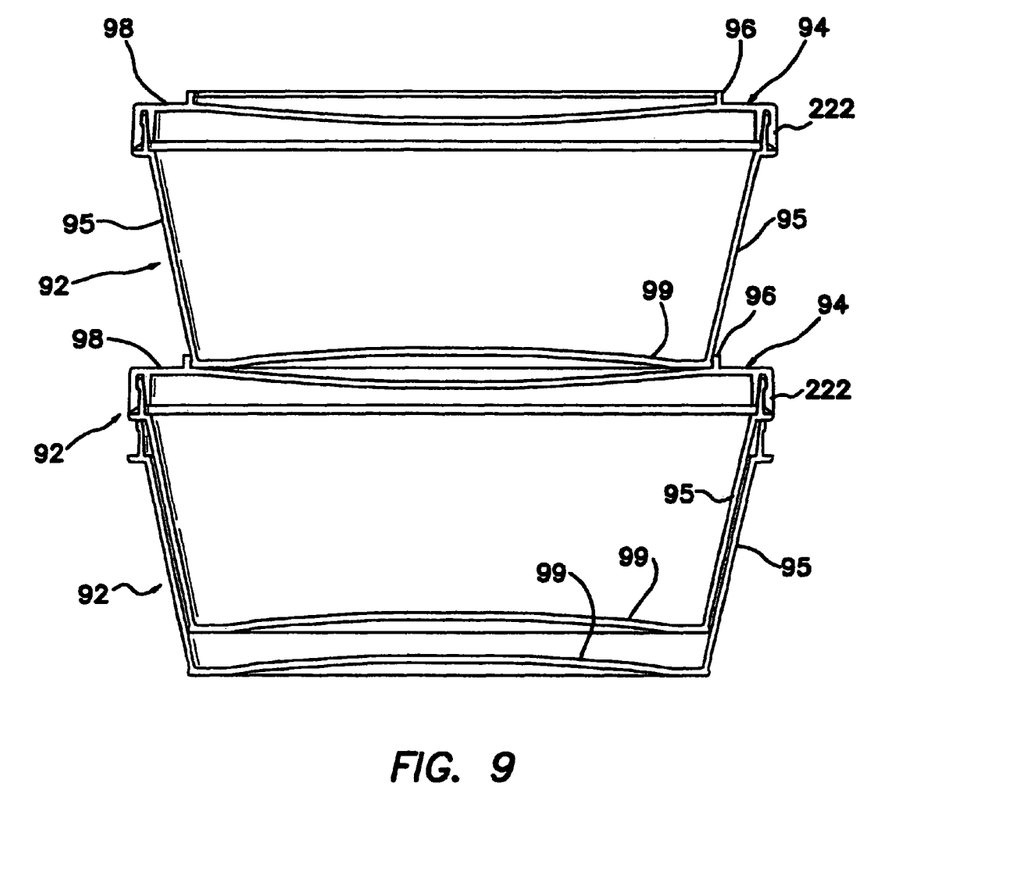
FIG. 9 is a cross-sectional view of a stack of containers with each of two of the containers including two elements coupled together and an embodiment of an assembly in accordance with the present invention, and with one container including an embodiment of one coupling member in accordance with the present invention.

FIG. 9 shows a stack of containers 92 which can be used, for example, as medical waste or hazardous waste containers. The containers 92 can be made of a suitable polymeric material, for example, a substantially inert polymeric material, a substantially non-reactive polymeric material and the like, such as polypropylene, polyethylene, ethylene/propylene copolymers, and the like. The containers 92 include a cover portion 94 including a first coupling member 222 extending continuously around the periphery of cover portion 94. The base or container portion 95 of each of the containers 92 includes a second coupling member 224 extending continuously around the periphery of the base portion 95.

The cover portion 94 of each of the containers 92 includes an annular upstanding projection 96 extending upwardly from the top surface 98 of the cover portion 94. The containers 92 are structured, e.g. tapered, so that the bottom 99 of each container can fit within the projection 96 of another of the containers 92 to provide a stack of containers, as shown with regard to the top two containers in FIG. 9. In addition, with the cover portion of the bottom most container 92 removed, the bottom two containers can be stacked together by inserting one container partially within the other container, also as shown in FIG. 9.

Thus, a series of containers 92 can be shipped, before and/or after being used to contain waste material, with the base portion being coupled to the cover portion using the first and second coupling members 222 and 224 in accordance with the present invention. Alternatively, the cover portions and the base portions can be coupled together at the use site.

Patents which may be useful in understanding certain aspects of the present invention include Martin, Jr. et al, U.S. Pat. No. 5,992,413; Clawson et al, U.S. Pat. No. 6,095,135; Clawson, U.S. Pat. No. 6,105,576; Clawson et al, U.S. Pat. 6,363,930; and Clawson et al, U.S. Pat. No. 6,415,788.

All patent applications and publications identified herein are incorporated in their entireties herein by reference.

While this invention has been described with respect to various specific examples and embodiments, it is to be understood that the invention is not limited thereto and that it can be variously practiced within the scope of the following claims.

What is claimed is:

1. An assembly for coupling together two elements, the assembly comprising:
a first coupling member located on a first element and having spaced apart first and second walls defining an opening, a hollow space therebetween and a closed end wall opposing the opening and extending from the first wall to the second wall, the first wall includes an inward step region away from the opening and extending away from the second wall at an angle relative to a region of the first wall closer to the opening, and a distal region extending from, and further away from the opening than, the inward step region; and
a second coupling member located on a second element and having a body fitted into the hollow space, the body includes a first surface having an outward step portion positioned at another angle relative to a portion of the first surface of the body closer to the opening, the angle being different in size relative to the other angle, and a second surface substantially opposing the first surface, wherein (a) the second wall includes only one outward step region, the outward step region located entirely further away from the opening than the inward step region and extending toward the first wall relative to a region of the second wall closer to the opening, or (b) the second surface includes only one outwardly projecting portion, the outwardly projecting portion positioned entirely further distally on the body relative to the outward step portion and extending away from the first surface relative to a more proximal region of the second surface, the second surface being in contact with the second wall at the outward step region or the outwardly projecting portion at a region of contact defined entirely by substantially a single contact line to deflect the body toward the first wall so that the outward step portion of the body moves into proximity to or into contact with the inward step region of the first wall and forms a seal between the first and second elements at the region of contact, and the body is not in contact with the first wall distal of the inward step region and is not in contact with the closed end wall.

2. The assembly of claim 1 wherein the second wall includes the outward step region.

3. The assembly of claim 1 wherein the second surface includes the outwardly projecting portion.

4. The assembly of claim 1 wherein the body of the second coupling member has a distal end which extends into the hollow space to a distance, and the second surface comes into resisting contact with the second wall at the outward step region or the outwardly projecting portion only after the distal end of the body is in the hollow space to an extent of at least about 75% of the distance.

5. The assembly of claim 1 wherein the assembly forms a hermetic seal between the first and second coupling members.

6. The assembly of claim 1 wherein an attempt to remove the body from the hollow space causes one or more visually observable alterations to at least one of the first and second coupling members.

7. The assembly of claim 1 wherein the first coupling member or the second coupling member further comprises at least one retention member retained in place relative to the first or second coupling member prior to the body being fitted into the hollow space.

8. The assembly of claim 1 wherein each of the first and second coupling members comprises a polymeric material and is molded.

9. The assembly of claim 1 wherein the angle is a substantially sharp acute angle, and the other angle is a substantially sharp acute angle.

10. The assembly of claim 1 wherein the outward step portion is in contact with the inward step region.

11. The assembly of claim 1 wherein the first and second coupling members are generally annular, substantially continuous and extend along or near peripheries of first and second elements, respectively.

12. The assembly of claim 1 which further comprises the first and second elements.

13. The assembly of claim 12 wherein the first and second elements are portions of an apparatus selected from the group consisting of containers, medical devices, filters, separators, heat exchangers, moisture exchangers, heat generators, moisture generators, gas absorbers, humidifier chambers, gas-liquid manifolds, valved manifolds, check valves, nebulizers, metered dose inhalers, sensor housings and water traps.

14. The assembly of claim 12 wherein the first and second elements are portions of an apparatus for treating respiratory gases in which the respiratory gases are treated to provide at least one of filtration, heat exchange, moisture exchange, heat generation and moisture generation.

15. The assembly of claim 1 wherein the assembly forms a hermetic seal between the first and second coupling members at pressures less than the yield point of the material of construction of one or both of the first and second coupling members.

16. The assembly of claim 1 which is structured so that the body cannot be non-destructively removed manually by human hands from the hollow space of the first coupling member.

17. An assembly for coupling together two elements, the assembly comprising:
a first coupling member located on a first element and having first and second walls defining an opening, a hollow space therebetween and a closed end wall opposing the opening and extending from the first wall to the second wall, the first wall defining an inward step region away from the opening and extending away from the second wall at an acute angle relative to a region of the first wall closer to the opening; and a second coupling member located on a second element and having a body fitted into the hollow space and including a first surface and a second surface substantially opposing the first surface, the first surface having an outward step portion extending away from the second surface at another acute angle relative to a portion of the first surface of the body closer to the opening, the first wall of the first coupling member defining a distal region extending from, and further away from the opening than, the inward step region, the second wall of the first coupling member including only one outward step region, the outward step region located entirely further away from the opening than is the inward step region and extending toward the first wall relative to a region of the second wall closer to the opening, the outward step region deflects the body toward the first wall so that the outward step portion of the body moves into proximity to or into contact with the inward step region of the first wall, and the second surface contacts the second wall at the outward step region at a region of contact defined only by substantially a single contact line and forms a seal between the first and second elements at the region of contact, and the body is not in contact with the first wall distal of the inward step region and is not in contact with the closed end wall.

18. The assembly of claim 17 wherein the first coupling member and the second coupling member are assembled together with substantially minimum resistance until the second surface comes into resisting contact with the second wall at the outward step region.

19. The assembly of claim 17 wherein the body of the second coupling member occupies at least a portion of the hollow space defined by the inward step region.

20. The assembly of claim 17 which further comprises the first and second elements.

21. The assembly of claim 20 wherein the first and second elements are portions of an apparatus for treating respiratory gases in which the respiratory gases are treated to provide at least one of filtration, heat exchange, moisture exchange, heat generation and moisture generation.

22. The assembly of claim 17 which is structured so that the body cannot be non-destructively removed manually by human hands from the hollow space of the first coupling member.

23. An assembly for coupling together two elements, the assembly comprising a first element having an opening, a first wall defining an inward step region away from the opening and a distal region extending from, and further away from the opening than, the inward step region, and a spaced apart second wall including only one outward step region, the outward step region located entirely further away from the opening than is the inward step region, and a closed end wall opposing the opening and extending from the first wall to the second wall, the inward step region extending away from the second wall at an acute angle relative to a region of the first wall closer to the opening; and a second element coupled to the first element and having a body including a first surface having an outward step portion positioned at another angle, different in size from the acute angle, relative to a portion of the first surface of the body closer to the opening, the outward step region of the first element being in contact with the body at a region of contact and bending the body of the second element toward the inward step region of the first element so that the outward step portion of the body moves into proximity to or into contact with the inward step region of the first wall and forms a seal between the first and second elements at the region of contact, the region of contact defined entirely by substantially a single contact line and the body is not in contact with the first wall distal of the inward step region and is not in contact with the closed end wall.

24. The assembly of claim 23 wherein the first and second elements are structured so that when an increased internal fluid pressure is generated tending to open the coupling of the first and second elements, the increased internal fluid pressure causes the seal between the first and second elements to be effective against increased fluid pressures relative to a seal between the first and second elements without the increased fluid pressure.

* * * * *